(12) United States Patent
Di Stasio et al.

(10) Patent No.: US 8,707,764 B1
(45) Date of Patent: Apr. 29, 2014

(54) ASSEMBLY AND METHOD FOR STANDARDIZED INSENSITIVE MUNITIONS TESTING

(75) Inventors: Anthony Di Stasio, New York, NY (US); Barry Fishburn, Dover, NJ (US); Sanjeev Singh, Dover, NJ (US); Rajen Patel, Iselin, NJ (US); Eugene Homentowski, Pequannock, NJ (US)

(73) Assignee: The United States of America as Represented by the Secretary of the Army, Washington, DC (US)

( * ) Notice: Subject to any disclaimer, the term of this patent is extended or adjusted under 35 U.S.C. 154(b) by 277 days.

(21) Appl. No.: 13/338,575

(22) Filed: Dec. 28, 2011

(51) Int. Cl.
 *G01N 33/22* (2006.01)
 *G01L 5/14* (2006.01)

(52) U.S. Cl.
 USPC ........................................ 73/35.14; 73/35.17

(58) Field of Classification Search
 USPC ............ 73/35.14, 35.16, 35.17, 12.01, 12.08, 73/12.09; 116/203, 207, 212
 See application file for complete search history.

(56) References Cited

U.S. PATENT DOCUMENTS

| | | | | |
|---|---|---|---|---|
| 4,881,400 | A * | 11/1989 | Goodman et al. | 73/709 |
| 6,131,437 | A * | 10/2000 | Sanford | 73/12.09 |
| 6,354,137 | B1 * | 3/2002 | Guirguis et al. | 73/35.17 |
| 6,925,887 | B1 * | 8/2005 | Coffey et al. | 73/774 |
| 7,225,691 | B2 * | 6/2007 | Tonooka et al. | 73/865.9 |
| 7,757,623 | B2 * | 7/2010 | Manahan | 116/203 |
| 7,975,527 | B2 * | 7/2011 | Manahan | 73/35.14 |
| 8,042,446 | B2 * | 10/2011 | Fujiwara et al. | 86/50 |
| 8,122,757 | B2 * | 2/2012 | Thompson et al. | 73/35.17 |
| 8,397,551 | B2 * | 3/2013 | King et al. | 73/35.14 |
| 2009/0013762 | A1 * | 1/2009 | Asahina et al. | 73/35.14 |
| 2012/0312076 | A1 * | 12/2012 | Fidelibus | 73/35.17 |

* cited by examiner

*Primary Examiner* — Helen Kwok
(74) *Attorney, Agent, or Firm* — Michael C. Sachs

(57) ABSTRACT

A test assembly for building a safety profile and a sensitivity profile of an explosive, by impacting the test assembly with a projectile. The safety profile of the explosive is built by determining a detonation threshold of the explosive in reaction to the projectile. The sensitivity profile is built by measuring a pressure difference between pressures acquired by the top sensor and the bottom sensor, resulting from a shock wave that travels through the explosive.

14 Claims, 7 Drawing Sheets

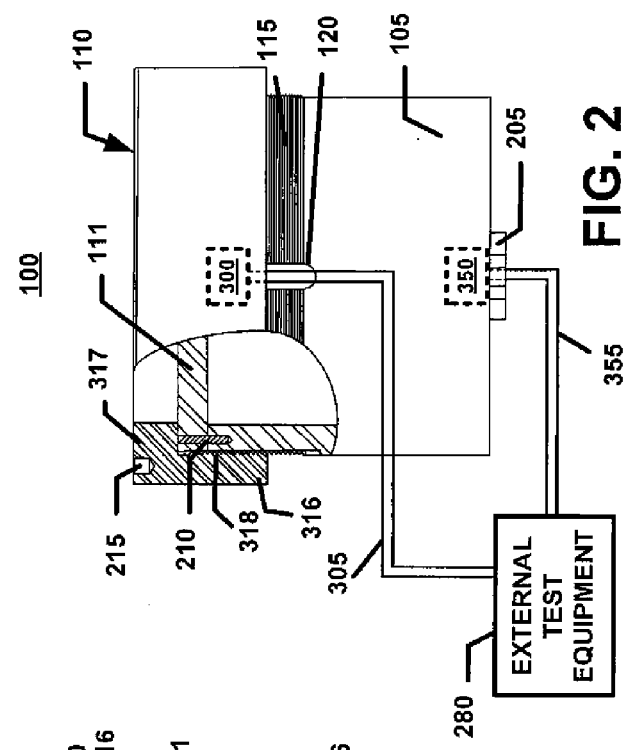
FIG. 3
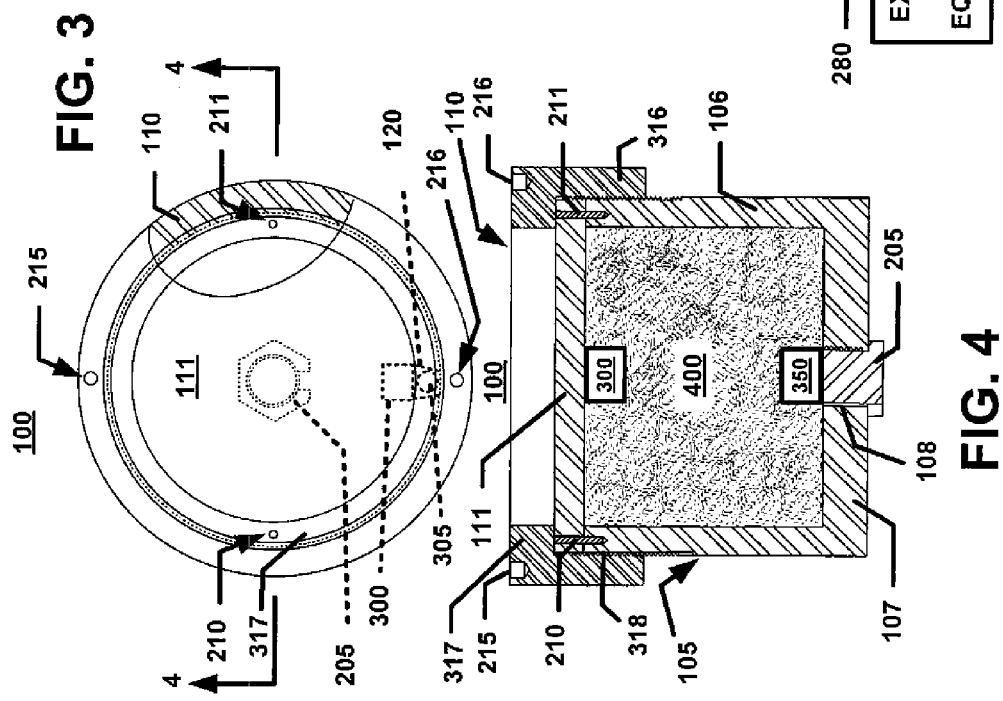
FIG. 2
FIG. 4

ASSEMBLY AND METHOD FOR STANDARDIZED INSENSITIVE MUNITIONS TESTING

GOVERNMENTAL INTEREST

The invention described herein may be manufactured and used by, or for the Government of the United States for governmental purposes without the payment of any royalties thereon.

FIELD OF THE INVENTION

The present invention relates in general to the field of munitions. More specifically, this invention relates to a relatively low cost, standardized, Insensitive Munitions (IM) testing of explosives for classification relative to safety and sensitivity.

BACKGROUND OF THE INVENTION

The development and production of Insensitive Munitions (IM) testing of explosives is very important and valuable to the armed forces. More specifically, explosive munitions must possess certain minimum safety requirements when under attack from thermal or other physical sources or threats.

Tactics such as redesigned or experimental munitions and less sensitive explosive fills are being continuously explored. In order to evaluate the effect of these changes to the munition, IM testing is used. IM testing generally includes taking a given munition and subjecting it to some stress, in order to simulate a hostile combat environment. For example, to simulate an impact from a fragment, a carefully shaped metal object is launched at the tested munition at 8,300 ft/second. IM testing is a critical part of the development of Insensitive Munitions.

IM Testing, while, quite necessary and important, it can be prohibitively expensive.

Extensive research has been conducted to implement methods according to which all munitions would be required to reach IM compliance. One method of achieving this goal is to replace the formulation within the explosive ordnance so that it is less sensitive to bullet or fragment impacts.

When a replacement formulation is desired, multiple candidates need to be evaluated. Normally, this is done using calculations and a relatively small scale testing. It would be desirable to have such testing correlate directly to real world threats. Although it would be desirable to have each new or experimental formulation tested, testing can be quite a time consuming, costly process, specifically if the round in question is rather large or expensive to produce.

What is therefore needed is a standardized test assembly and method of use, which is relatively simple and inexpensive to implement. Prior to the advent of the present invention, the need for such a standardized test assembly and procedure has heretofore remained unsatisfied.

SUMMARY OF THE INVENTION

The present invention satisfies this need, and describes a standardized test assembly and method of use the same. The test assembly provides a standard protocol for rating explosive response.

The test assembly (or test device) simulates a munition for IM testing purposes, and is relatively simple and inexpensive to implement.

The test assembly provides a controlled repeatable way of obtaining data for comparison and ranking, and thus reduces problems associated with errors at the impact point.

The test assembly is designed to maintain confinement after impact. It simplifies loading and testing of new or experimental energetic explosives.

The test assembly provides data that is vital to increase the accuracy of present shock models.

The test assembly provides a cost and schedule effective way of explosive down-selection for new end items.

The robust design of the test assembly makes it capable of testing multiple items for explosive implementation.

Consequently, the test assembly enables an efficient down-selection of explosives, resulting in the following advantages:

It directly correlates an explosive response in an end item.

It validates CALE and ALE 3-D (FI) modeling and simulation.

It increases confidence level of IM testing.

It provides a cost-effective way to load and test multiple times.

Its axial symmetry facilitates modeling in order to determine the proper dimensions according to which the sidewalls would be unlikely to produce strong reflections or significant focusing.

It further improves the quality and accuracy of conventional modeling efforts.

Its vessel design maintains the integrity of the test assembly so that the explosive remains under confinement (with the exception of a penetration hole). A side wall houses a gage that remains secure until a reaction violence shatters the vessel.

It enables a relatively simple way to interchange the cover plates.

It enables the use of pressure gauges and impact plates of varying thicknesses, in order to accurately assess an explosive's response to bullet impact, fragment impact, and sympathetic detonation.

It can be used to optimize candidate groups for possible implementation.

The foregoing and additional features and advantages of the present invention are realized by a standardized test assembly that generally includes, in a preferred embodiment, a one half inch steel cylinder with interchangeable plates on one open end that is impacted by the testing projectile. The plates are interchangeable so plates of varying thicknesses can be used, thus altering the amount of shock imparted into an explosive munition.

The test assembly presents a relatively inexpensive alternative to narrow down and select the optimal candidate explosives that will perform according to desired specifications. The test assembly can be used to evaluate the validity of shock initiation and detonation models and can greatly increase the confidence level of IM testing.

The test assembly is highly flexible, and is capable of replicating numerous types of munitions that can be loaded as melt pours, pressed munitions, or cast cure items.

To this end, a principal goal of the present test assembly is to distinguish if the event is primarily shock driven or if the shock just sets up damage region that subsequently explodes. In the former case, formulators would concentrate on reducing shock sensitivity, while in the latter case, formulators would likely consider softening their formulation, making it less brittle.

By analyzing pressure data obtained by top and bottom sensors (or gauges), the test assembly provides an understanding of the cause of violence in non-detonation explosion, thus enabling the determination of alternative ways for altering the explosives formulations in order to mitigate this effect.

The test assembly enables the use of generic hardware (GH) to augment testing, in order to improve the confidence level of explosive reaction using statistical analysis.

BRIEF DESCRIPTION OF THE DRAWINGS

The above and other features of the present invention and the manner of attaining them, will become apparent, and the invention itself will be best understood, by reference to the following description and the accompanying drawings, wherein:

FIG. 2 is a partly cutaway, side elevational view of the test assembly of FIG. 1;

FIG. 3 is a partly cutaway, top view of the test assembly of FIGS. 1 and 2;

FIG. 4 is a cross-sectional, side elevational view of the test assembly of FIGS. 1-3, taken along line 4-4 of FIG. 3;

Similar numerals refer to similar elements in the drawings. It should be understood that the sizes of the different components in the figures are not necessarily in exact proportion or to scale, and are shown for visual clarity and for the purpose of explanation.

DETAILED DESCRIPTION OF PREFERRED EMBODIMENTS

Figure 1:
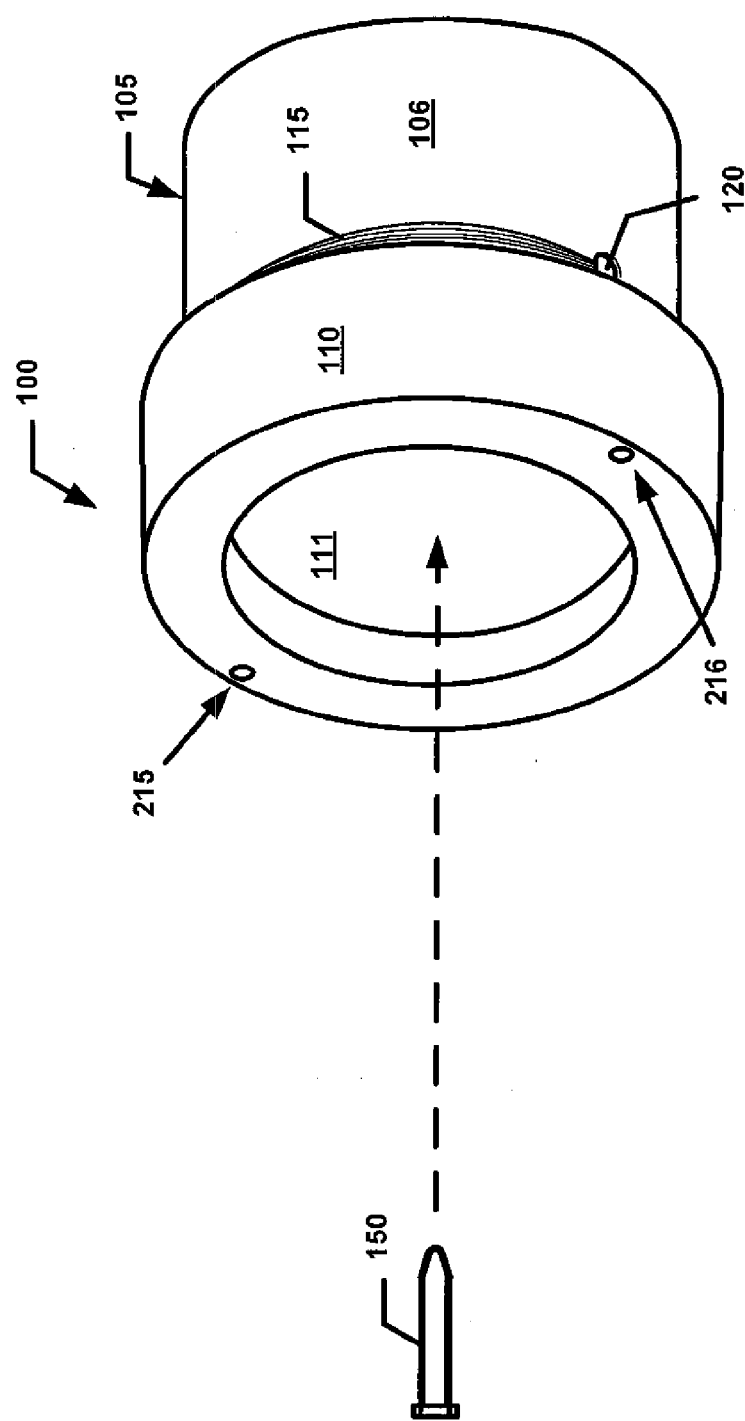
FIG. 1 is a perspective view of a test assembly of the present invention, shown targeted by a projectile, in order to test an explosive within a vessel that forms part of the test assembly.

FIG. 1 is a perspective view of a test assembly 100 of the present invention, shown targeted by a projectile 150, in order to test an explosive 400 (FIG. 4) stored within the test assembly 100. The test assembly 100 provides a standardized method for ranking different explosives in terms of sensitivity and safety.

The test assembly 100 is generally formed of a vessel 105 with an open top end and a partially open bottom end, as it will be explained later in greater detail. The top end is closed by an impact plate 111 that is maintained in a hermetically locked position against the vessel 105 by means of a top cap 110. The bottom end of the test assembly 100 is hermetically sealed with a bottom plug 205 (FIG. 2).

As further illustrated in FIGS. 2, 3, and 4, a top sensor 300 is located near the top end of the vessel 105 and is connected to external test equipment (or computer) 280 by means of a cable 305. Similarly, a bottom sensor 350 is located near the bottom end of the vessel 105, and is connected to the external test equipment 280 by means of a cable 355. The external test equipment 280 interprets the measurements acquired by the top and bottom sensors 300, 350, in order to assist in ranking the explosive 400 being tested.

In operation, the bottom sensor 350 is inserted at or near the bottom end of the vessel 105, and the bottom plug 205 is screwed onto the vessel 105 to provide a tight closure. The explosive 400 to be tested is then packed inside the vessel 105 to fill the entire internal volume of the body 106. The top sensor 300 is the inserted at or near the top end of the vessel 105, and the impact plate 111 is placed on the vessel 105. A top cap 110 is then screwed onto the vessel 105 to provide a tight closure.

The projectile 150 is then aimed and shot at the impact plate 111. A principal objective of the present test assembly 100 is to determine if the event is primarily shock driven or if the shock just sets up damage region that subsequently explodes. In the event it is determined that the event is primarily shock driven, formulators in the external test equipment 280 would concentrate on reducing shock sensitivity. On the other hand, if it is determined that the shock just sets up damage region that subsequently explodes, formulators in the external test equipment 280 would likely consider softening their formulation, making the final material more robust and less brittle.

The external test equipment 280 analyzes the pressure data acquired by the top and bottom sensors 300, 350, so that the test assembly 100 provides an understanding of the cause of violence in non-detonation explosion, thus enabling the determination of alternative ways for altering the explosives formulations in order to mitigate this effect.

Figure 5:
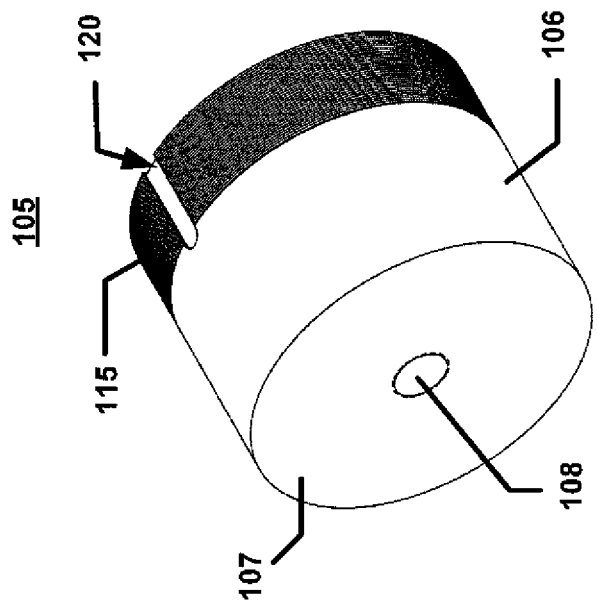
FIG. 5 is a perspective view of a vessel that forms part of the test assembly of FIG. 1, showing a top lateral access channel.
Figure 6:
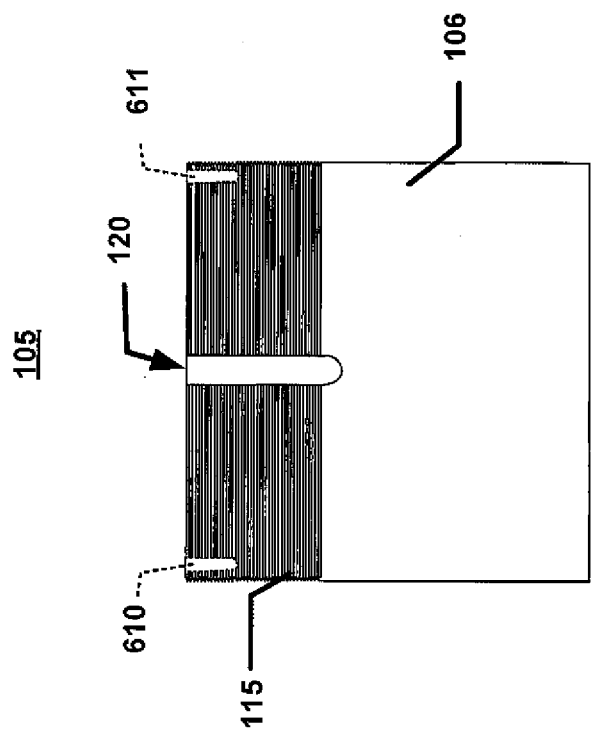
FIG. 6 is a side elevational view of the vessel of FIG. 5.

Considering now the individual components of the test assembly 100 in more detail, FIGS. 5 and 6 illustrate an exemplary vessel 105. The vessel 105 is integrally formed of a generally cylindrical body 106 with an open top end, and which terminates at its bottom end into a bottom 107. While the body 106 is described herein as having a cylindrical shape, it should be understandable that different shaped might be alternatively used.

The bottom 107 is generally disc shaped, having a central bottom threaded access opening 108 for mating with the bottom plug 205. While the access opening 108 is shown as extending through the bottom 107, it should be understood that the access opening 108 could be disposed at a different suitable location along the body 106.

The top end of the body 106 includes an externally threaded section 115 that allows it to threadably secure the body and the impact plate 111 to the top cap 110. The threaded section 115 is chamfered into a top lateral access channel or groove 120 that accommodates the conductor (or cable) 305 of the top sensor 300, to enable external access to the top sensor 300, which is inserted within the body 106.

The periphery of the top end of the body 106 is provided with two alignment holes 610, 611, that are designed and disposed so that they align with corresponding alignment through holes 710, 711 in the impact plate 111 (FIGS. 7, 8, 9), in order to enable dowel pins 210, 211 (FIGS. 2, 3, 4) to be inserted therethrough, for preventing the rotational movement of the impact plate 111.

In this particular embodiment the vessel 105 has a uniform thickness that ranges between, for example only, approximately 0.490 in and 0.510 in. The body 106 has an outer diameter of, for example, 6 inches, and an inner diameter of, for example 5 inches. The height of the body is approximately 5 inches. The threaded section 115 is preferably, approximately 1.5 in wide. The bottom threaded access opening 108 is generally circularly shaped with a diameter of preferably, approximately 1.00 in. It should be understood that different tests might require other shapes and dimensions of the vessel 105 and its components, which are foreseeable within the scope of the present invention.

The vessel 105 and the main components of the test assembly 100 are made of any suitable material that can withstand anything less severe than a deflagration (fast burning reaction). An exemplary material would be steel, such as steel 4340. The dowel pins 210, 211 are preferably made of steel 1080.

When testing the explosive 400, the projectile 150 is fired directly at the impact plate 11, in order to generate a shock wave that travels axially through the impact plate 111 and then through the explosive 400. It would be desirable that the vessel 105 remain intact so that the shock wave generated by the impacting projectile 150 has time to reach the bottom 107 of the vessel 105 where the bottom sensor 350 is located.

In an exemplary embodiment, the top sensor 300 and the bottom sensor 350 are preferably pressure sensors. It should however be understood that other sensors might alternatively be used. As an example, the top and/or bottom sensors 300, 350 may be MnCn, PDV, PVDF, Crush, etc. sensors.

Figure 7:
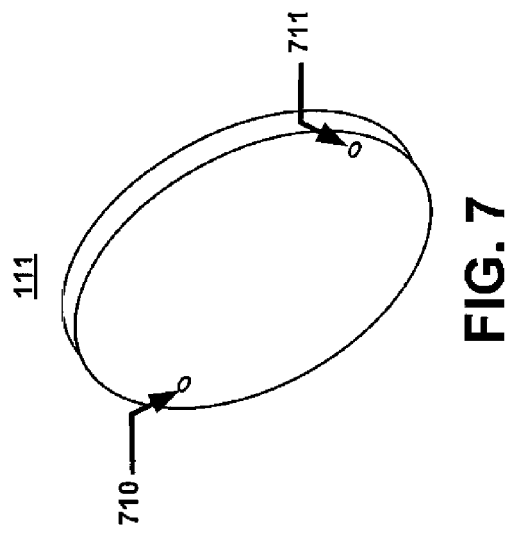
FIG. 7 is a perspective view of an impact plate that forms part of the test assembly of FIGS. 1-4.
Figure 8:
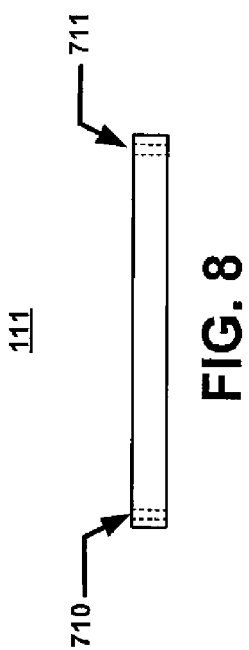
FIG. 8 is a side elevational view of the impact plate of FIG. 7.
Figure 9:
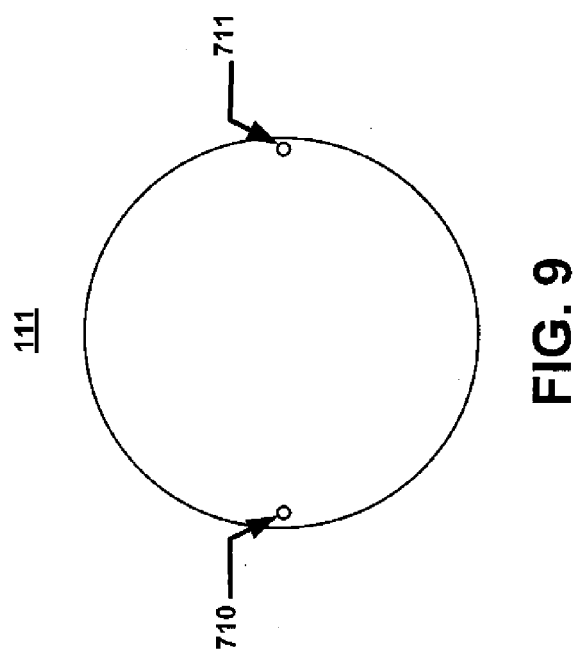
FIG. 9 is a top view of the impact plate of FIGS. 7 and 8.

FIGS. 7, 8, and 9 illustrate the impact plate 111 as being disc shaped (or cylindrically shaped) with a diameter that matches the diameter of the top end of the body 106 to enable a smooth closure when capped by the top cap 110. The impact plate 111 is made of the same or similar material as the vessel 105, for example solid steel, in order to preserve the integrity of the test assembly 100.

The thickness of the impact plate 111 can vary, depending on the test and type of munition being simulated. For illustration purpose, the thickness of the impact plate 111 can vary from approximately 0.002 in to 2.00 in.

The impact plate 111 includes two alignment through holes 710, 711 to lock the impact plate 111 in place (i.e., to prevent its rotational movement). In the present preferred embodiment, the through holes 710, 711 are illustrated as being diametrically oppositely disposed. It should be understood that a different number of through holes 710, 711 can be disposed at different locations around the periphery of the impact plate 111.

Upon assembly, the impact plate 111 is simply placed on the top of the body 106 and the load of explosive 400, the through holes 710, 711 are aligned with the holes 610, 611, and the dowel pins 210, 211 are inserted therethrough, as shown in FIGS. 2, 3, 4, to prevent the rotational movement of the impact plate 111.

Figure 10:
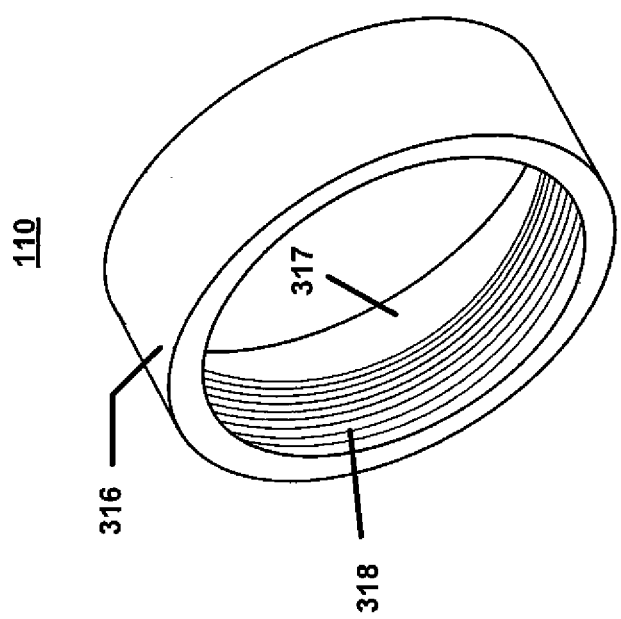
FIG. 10 is a perspective view of a top cap that forms part of the test assembly of FIGS. 1-4.
Figure 11:
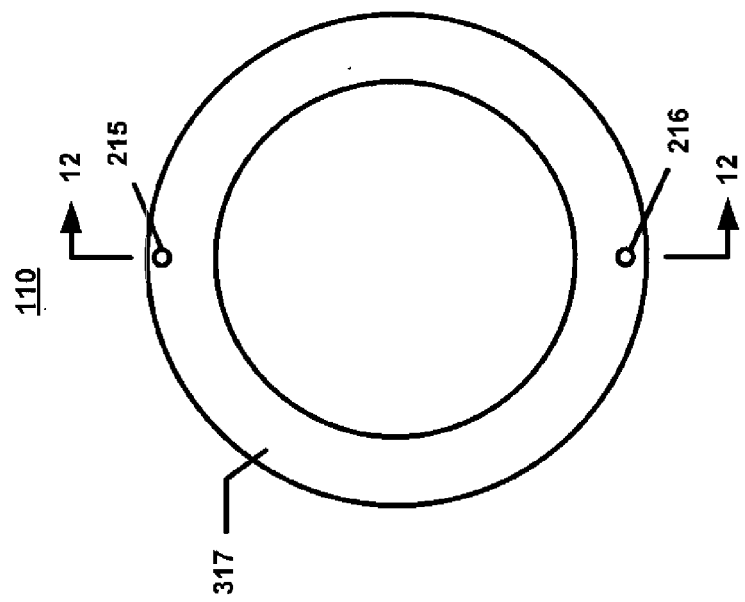
FIG. 11 is a top view of the top cap of FIG. 10.
Figure 12:
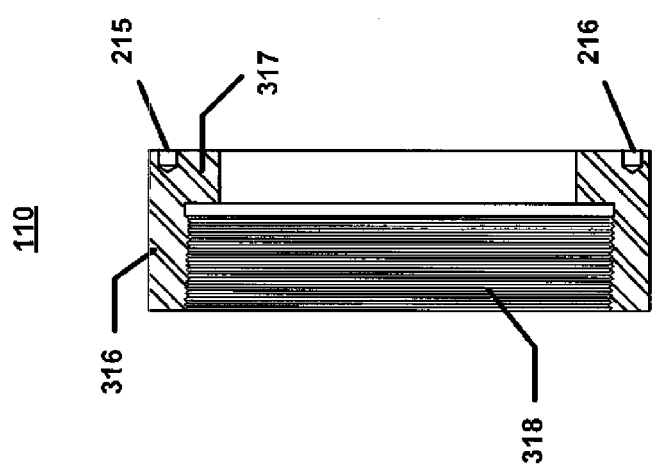
FIG. 12 is a cross-sectional, side view of the top cap of FIGS. 10 and 11, taken along line 12-12 of FIG. 11.

FIGS. 10, 11, 12 illustrate an exemplary top cap 110. The top cap 110 is integrally formed of a cylindrical ring 316 that extends inwardly, at a first end, into a flange 317. The flange 317 forms an annular band (or ledge) and a central opening that permits access to the impact plate 111 (i.e., that exposes the impact plate 111 to the projectile 150). The second end of the ring 316 and is dimensioned to be threaded onto the top end of the vessel body 106, by means of matching internal threads 318 (FIGS. 2, 3), in order to securely lock the top cap 110 and the impact plate 111 to the vessel 105.

Two wrench holes 215, 216 are formed in the flange 317 to enable the further tightening of the top cap 110 to the vessel 105. In an exemplary embodiment, the width of the flange 317 ranges between approximately 0.400 in and 0.500 in.

Figure 13:
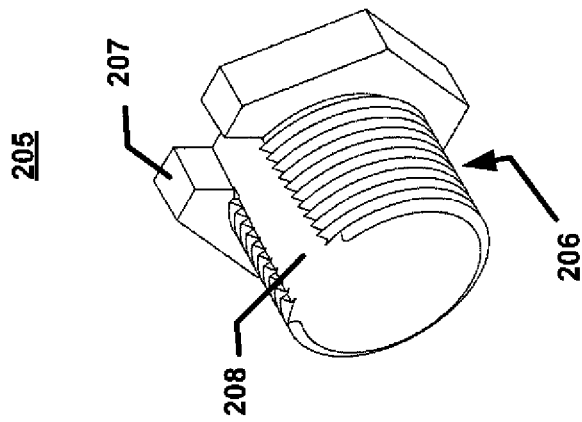
FIG. 13 is a perspective view of a bottom plug that forms part of the test assembly of FIGS. 1-4, showing a bottom access channel.
Figure 14:
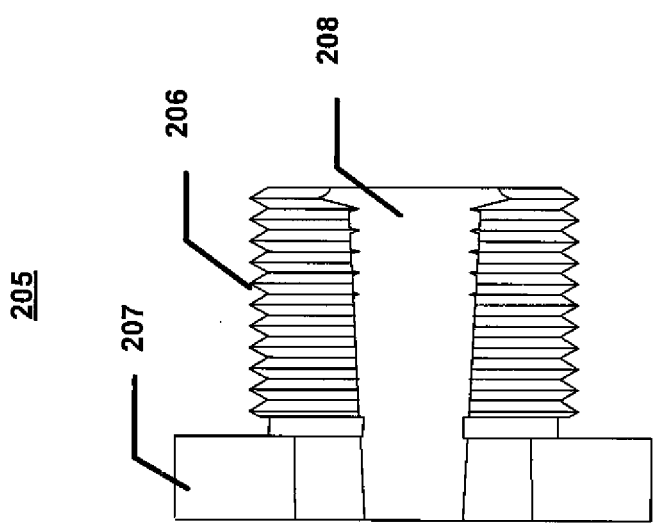
FIG. 14 is a side view of the bottom plug of FIG. 13.

FIGS. 13, 14 illustrate the bottom plug 205 that is integrally formed of a threaded shaft 206 and a head 207. A bottom access channel 208 is formed through the shaft 206 and the head 207, to permit access to the interior chamber formed by the vessel body 106.

Upon assembly and as further illustrated in FIGS. 2, 3, 4, the bottom sensor 350 is placed on the bottom 107 of the vessel 105 and the cable 355 is extended through the bottom threaded access opening 108 and along the bottom access channel 208 of the bottom plug 205. The bottom plug 205 is then threaded onto the bottom 107.

The present test assembly 100 enables the identification of the safety and sensitivity of the explosive 400 being tested. Safety is assessed by the reaction of the explosive 400 to the impacting projectile (or a given threat) 150. If the explosive 400 reaction falls outside the allowed limits, the explosive 400 would be determined to be unsafe. The safety profile of the explosive 400 can then be built by determining a detonation threshold of the explosive 400 in reaction to the impacting projectile 150.

The sensitivity that characterizes the explosive 400 is defined as the level of pressure or energy that is required to detonate the explosive 400. According to the present invention, sensitivity is measured with the pressure sensors 300, 350 that measure the pressure difference between the pressures measured by the top sensor 300 and the bottom sensor 350, due to the shock wave that travels through the explosive 400.

The measured pressure difference is then compared to the actual reaction of the explosive 400 that can be, for example visually determined. As an example, in a first test, the measured pressure difference for a particular explosive 400 is approximately ±50 kBar and the explosive 400 did not detonate. The test is repeated several times, using different threats or projectiles 150 and the pressure differences are measured, and the reactions of the explosive 400 are noted, particularly those pressure differences that trigger the detonation of the explosive 400.

Consequently, the test assembly 100 enables the experimenter to build accurate safety and sensitivity profiles for the explosive 400, in a very efficient and economical way.

It should be understood that other modifications may be made to the present design without departing from the spirit and scope of the invention.

What is claimed is:

1. A test assembly for building a safety profile and a sensitivity profile of an explosive, by impacting the test assembly with a projectile, comprising:
    a vessel having an open top end and a bottom end;
    an impact plate that fits on the top end of the vessel;
    a top cap that is secured to the top end of the vessel for maintaining the impact plate in a hermetically locked position against the vessel;
    a top sensor that is disposed in proximity to the impact plate; and
    a bottom sensor that is disposed in proximity to the bottom end of the vessel;
    wherein the safety profile of the explosive is built by determining a detonation threshold of the explosive in reaction to the projectile that collides with the impact plate; and
    wherein the sensitivity profile of the explosive is built by measuring a pressure difference between pressures acquired by the top sensor and the bottom sensor, resulting from a shock wave that travels through the explosive.

2. The test assembly of claim 1, wherein the measured pressure difference is compared to a determinable reaction of the explosive.

3. The test assembly of claim 2, wherein the bottom end of the vessel is partially open.

4. The test assembly of claim 3, wherein the bottom end of the vessel is hermetically sealed with a bottom plug.

5. The test assembly of claim 4, wherein the bottom sensor is accessed through an access channel formed in the bottom plug.

6. The test assembly of claim 5, wherein the vessel includes a body and an externally threaded section that allows the body to be threadably secured to the impact plate to the top cap.

7. The test assembly of claim 6, wherein the threaded section of the body includes a top access channel; and
   wherein the top sensor is accessed through the top access channel.

8. The test assembly of claim 7, wherein the body is generally cylindrically shaped.

9. The test assembly of claim 8, wherein the top sensor is a pressure sensor.

10. The test assembly of claim 8, wherein the bottom sensor is a pressure sensor.

11. The test assembly of claim 8, wherein the impact plate includes a cylindrically shaped disc.

12. The test assembly of claim 8, wherein the impact plate includes at least one alignment hole to prevent a rotational movement of the impact plate.

13. The test assembly of claim 8, wherein the top cap is integrally formed of a ring that extends into a flange and a central opening that exposes the impact plate to the projectile.

14. The test assembly of claim 13, wherein the flange forms an annular band; and
   wherein the ring is securely locked to the vessel.

* * * * *